(12) United States Patent
Shimada et al.

(10) Patent No.: US 6,554,444 B2
(45) Date of Patent: Apr. 29, 2003

(54) GAZING POINT ILLUMINATING DEVICE

(75) Inventors: Jun-ichi Shimada, Kyoto (JP); Yoichi Kawakami, Kusatsu (JP); Shigeo Fujita, Kyoto (JP)

(73) Assignee: Kansai Technology Licensing Organization Co., Ltd., Kyoto (JP)

( * ) Notice: Subject to any disclaimer, the term of this patent is extended or adjusted under 35 U.S.C. 154(b) by 86 days.

(21) Appl. No.: 09/798,982

(22) Filed: Mar. 6, 2001

(65) Prior Publication Data

US 2001/0021108 A1 Sep. 13, 2001

(30) Foreign Application Priority Data

Mar. 13, 2000 (JP) .......................... 2000-068696
Aug. 29, 2000 (JP) .......................... 2000-259771

(51) Int. Cl.[7] .............................. F21V 21/08
(52) U.S. Cl. ................ 362/103; 362/231; 362/230; 362/276; 362/295; 362/84
(58) Field of Search ............... 362/103, 105, 362/106, 230–231, 276, 295, 84

(56) References Cited

U.S. PATENT DOCUMENTS

| 4,234,910 A | * | 11/1980 | Price .......................... 362/105 |
| 4,254,451 A | | 3/1981 | Cochran, Jr. |
| 4,616,257 A | * | 10/1986 | Kloots et al. ................ 362/253 |
| 4,759,615 A | * | 7/1988 | Bainbridge et al. .......... 362/103 |
| 5,289,355 A | * | 2/1994 | Cimock ......................... 362/86 |
| 5,355,285 A | * | 10/1994 | Hicks .......................... 362/105 |
| 5,430,620 A | | 7/1995 | Li et al. |
| 5,722,762 A | | 3/1998 | Soll |
| 6,014,524 A | | 1/2000 | Suzuki et al. |
| 6,139,172 A | * | 10/2000 | Bos et al. ..................... 362/494 |
| 6,224,227 B1 | * | 5/2001 | Klootz ......................... 362/105 |
| 6,390,640 B1 | * | 5/2002 | Wong et al. .................. 362/105 |

FOREIGN PATENT DOCUMENTS

| JP | S56-156022 | 4/1955 |
| JP | S57-22720 | 7/1955 |
| JP | H6-7702 | 2/1994 |
| JP | H8-46833 | 2/1996 |
| JP | 3049423 | 3/1998 |
| JP | 2000-39595 | 2/2000 |
| WO | WO 99/65381 | 12/1999 |

* cited by examiner

Primary Examiner—Sandra O'Shea
Assistant Examiner—Ronald E. DelGizzi
(74) Attorney, Agent, or Firm—Oliff & Berridge, PLC (57) ABSTRACT

A gazing point illuminating device is provided with: a light source; a direction changing mechanism for changing the lighting direction of the light source; a gazing direction detector for detecting the direction of the user's gazing line; and a controller for changing the lighting direction corresponding to the detected gazing direction. When, LEDs are used as the light source, and the light source is attached to the goggles worn by a user, the goggles can be useful gazing point illuminating device by themselves even if they do not include gazing point or direction detectors, because a person normally look straight ahead except for unusual occasions where he/she purposefully avert his/her gaze. Thus, an illuminating device fixed to a person's head for lighting forward is a gazing point illuminating device. It is preferred to provide an LED panel at the left and right ends of goggles.

10 Claims, 9 Drawing Sheets

GAZING POINT ILLUMINATING DEVICE

The present invention relates to a multi-purpose gazing point illuminating device which can change the lighting direction corresponding to the gazing direction of the user. It further relates to a surgical operation illuminating system that uses the same device.

BACKGROUND OF THE INVENTION

For a light in an operation room of a hospital, a so-called astral lighting system has been used to illuminate the part of operation with high illuminance without casting shadows there.

An astral lighting system is constructed so that many lamps are embedded in a large dish-like base which is suspended from the ceiling of the operation room. Therefore, for its placement, a large room is needed and the ceiling of the operation room must be adequately high. Furthermore, because of its very heavy weight, not only the ceiling but also the whole operation room is required to be structurally strong. As a result, the construction cost of an operation room is high due to this lighting system.

Another problem of the astral lighting system is that it generates a large amount of heat. In a heart operation, however, the temperature of the patient's body must be kept low. In such case, a high-power cooling system must be provided to overcome the heat caused by the lighting system and lower the body temperature in a short time. This also has increased the construction cost of the operation room.

Figure 11:
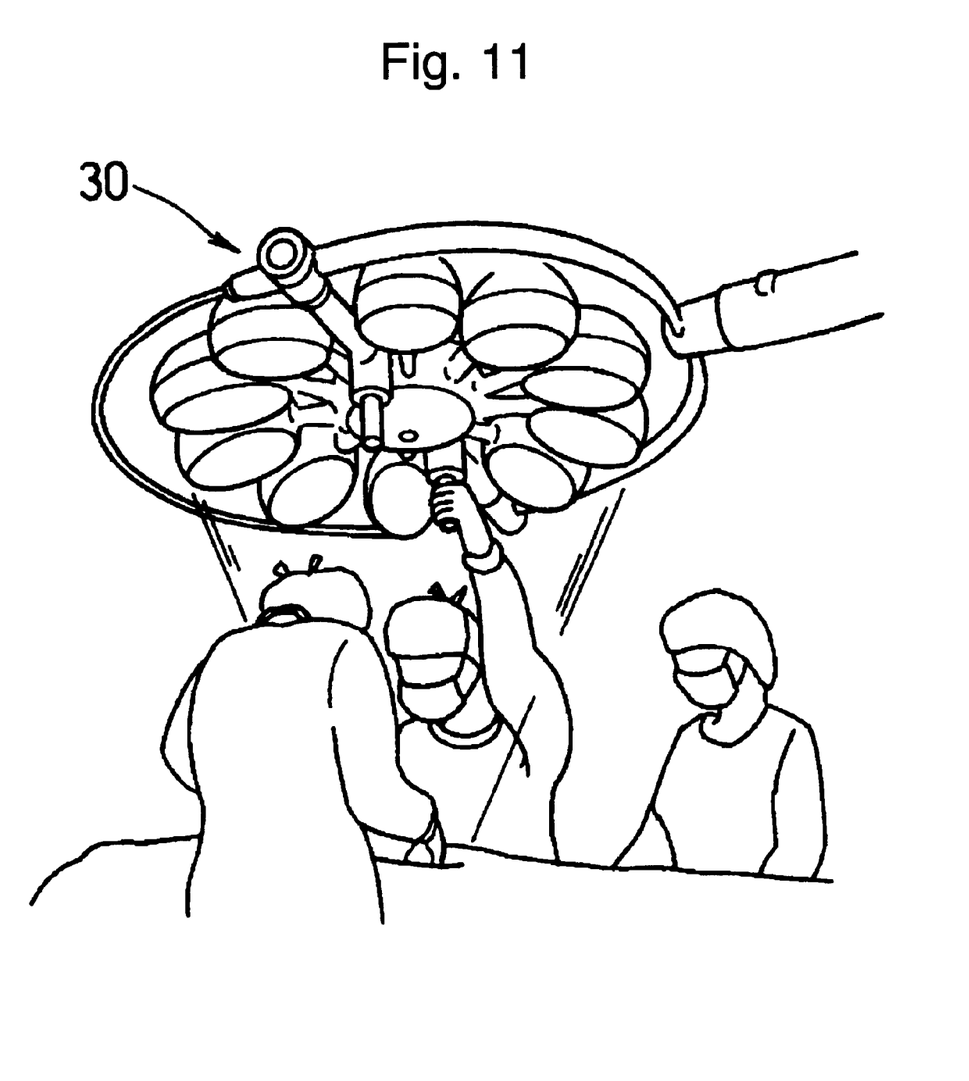
FIG. 11 is a view of a conventional surgical operation illuminating system.

When an operation is performed, several people including operation doctors and assisting staff stand by the operation bed, as shown in FIG. 11. In a culmination or an important time of an operation, they tend to unconsciously lean forward to gaze the part of operation, so that their heads intercept the light from the astral lighting system 30 to the part of operation, making a shadow on the part.

In a certain kind of operation, an operator needs to look at the part of operation from the side, not from the high as shown in FIG. 11. For example, in an operation for a colon tumor, the operator needs to look at the anal from side. In this case, in addition to the astral lighting system on the ceiling, another side lighting system is necessary to directly illuminate the part. Since it is normally impossible to use a side lamp as large as the astral lighting system on the ceiling, the operator is sometimes required to take a clumsy or unnatural position for avoiding his own shadow cast on the part of operation.

It has already been proposed to fix a lamp to the operator's head. Or a device has been proposed in which an end of an optical fiber bundle is fixed to the operator's head and a beam of light from a remote light source is transmitted therethrough. Since, in these cases, the lamp or the light emitting end of the fiber bundle is fixed to the operator's head, he/she must change the position of his/her head when he/she wants to change the illuminating direction. When an operation takes a long time, the operator needs to change his/her head position frequently or needs to take and keep clumsy postures for a certain period of time, which causes an excessive fatigue in his/her neck or shoulder.

Besides the above-mentioned surgical operation, it is also convenient if, in the case of a home medical care or a nursing care, the lighting direction can be changed freely corresponding to the part to be cared. Especially in the home medical care case, an easy and portable device that can illuminate a necessary point is required because conventional lighting systems are hard to carry around.

SUMMARY OF THE INVENTION

The present invention is achieved in this respect placing its primary object to provide a gazing point illuminating device that can light in a desired direction easily and illuminate an object point without making a shadow. Another object is to provide a portable gazing point illuminating device for illuminating a desired point without requiring a clumsy posture of the user. Preferably it can be used in a surgical operation.

According to the present invention, a gazing point illuminating device is provided with: a light source; a direction changing mechanism for changing the lighting direction of the light source; a gazing direction detector for detecting the direction of the user's gazing line; and a controller for changing the lighting direction corresponding to the detected gazing direction.

In the present invention, the user's gazing direction is detected and the lighting direction of the light source is changed corresponding to the detected gazing direction, so that the gazing point of the user is always illuminated automatically. When the device is used in a surgical operation, for example, the operating doctor need not take a clumsy posture as was conventionally required, and the part of operation can be illuminated assuredly and safely. When the device is used in the case of a home medical care or a nursing care, the part to be cared can be illuminated according to the doctor's or care-taker's gazing direction.

In a style of the present invention, an EL (Electro-Luminescence) panel may be used as the light source. An EL panel is a lighting device using a thin-film electroluminescent element. There are two types in the EL panels: an inorganic EL type and an organic EL type. The inorganic EL type includes those using manganese added zinc sulfide (ZnS:Mn), terbium added zinc sulfide (ZnS:Tb), cerium added strontium sulfide (SrS:Ce), cerium added strontium thiogallate (SrGa2S4:Ce), etc. The organic EL type includes those using tetraphenyl-diamine derivatives (TPD), polyvinyl-carbazole (PVK), aluminum-quinolinol complex (Alq3), distyryl-biphenyl derivatives (DPVBi), etc. The EL panel used in the present invention may be shaped flat or concave against the lighting direction. When it is shaped concave so that the light from the whole EL panel is converged to an object point or object area, the illuminating efficiency is very high.

In another style of the present invention, the light source may be an LED (Light Emitting Diode) panel in which an LED or a plurality of LEDs are arranged on a base board. The number of LEDs on an LED panel depends on the strength of the LED used and the brightness needed by the illuminating device using the LED panel. When a plurality of LEDs are used, they may be arranged on the base board one-dimensionally (straight or curve) or two-dimensionally. The base board can be flat or concave against the lighting direction, as described above for the EL panel.

An LED has a high energy-converting efficiency. Compared to conventional incandescent lamps, its energy consumption is greatly reduced and the heat generation is thus minimized. When it is used in a surgical operation where the part of operation needs to be cooled, the operation can be performed without a powerful cooling system.

An LED has other great advantages of longlife and lightweight. The illuminating device of the present invention using an LED panel also has the same advantages over conventional illuminating devices. When the gazing point illuminating device of the present invention is used in a surgical operation, the cost can be greatly reduced compared to the conventional astral lighting system which claims a large construction cost and requires a costly cooling system.

When an LED panel is used in the present invention, white LED or LEDs may be used. In this way, the illuminating device of the present invention realizes an energy-saving, lightweight and longlife white light source which can replace conventional incandescent lamps or fluorescent lamps.

White LEDs can be fabricated either by the combination of LEDs emitting at blue, green and red spectral range, or by the combination of blue LEDs and phosphors. Latter type of white LEDs, for example, consist of InGaN-based LED and YAG-phosphor, whose spectra are composed of two emission bands, where the blue band peaking at 460 nm is the emission from InGaN quantum-well-active layers, and the broad yellow band at 560 nm is the one from YAG phosphor.

When an LED panel is used in the present invention, the LED panel may be composed of a set or a plurality of sets consisting of a red (R) LED, a green (G) LED and a (B) LED. By presetting the respective lighting strengths of the R, G and B LEDs, light of a desired color can be obtained. When it is used for a surgical operation or for a home medical care purpose, the strengths of the three primary colors can be preset so that the color of the skin or blood looks natural.

When the LEDs are used in a medical field, the intensity distribution in the red spectral region is very important to render inherent color of raw flesh such as skin, blood, fat tissue and internal organs. This can be achieved by adding red LEDs in the array of white LEDs or white LED chips.

When an LED panel is used in the present invention, the LED panel may include an ultraviolet LED or LEDs. In this way, the ultraviolet light from the illuminating device of the present invention excites a fluorescent signing attached to an object beforehand. When it is used in a surgical operation, morbid parts, such as a tumor, attached by a fluorescent signing can be made exclusively visible. The ultraviolet LEDs may be used alone, with white LEDs or with the RGB LEDs in the LED panel. When LEDs of different kinds are used in combination, all kinds of LEDs may be lit simultaneously, or they may be switched depending on the situation or purpose of illumination.

When an LED panel is used in the present invention, LEDs placed on the base board may be packaged type LEDs or chip type LEDs. An LED itself is as small as 0.5 mm or less. For general use of an LED as a light source, for the purpose of protecting the LED, safety, and convenience of handling, an LED is normally packaged in a cannonball-shaped transparent plastic case of about several millimeters with two lead wires drawn outside. For the gazing point illuminating device of the present invention, such individually packaged LEDs may be used, or alternatively, the chip type LEDs may be used. When the chip type LEDs are used, the size and area of the LED panel can be far smaller than that using individually packaged LEDs for the same light emitting strength. This leads to a smaller light source and thus to a far smaller, lightweight gazing point illuminating device.

The illuminating device of the present invention may include a dimming controller for changing the lighting strength of the light source, whereby the gazing object can be illuminated at an arbitrary illuminance. When the light source includes LEDs of various colors (including the case where ultraviolet LEDs are included), it is preferable to control the lighting strengths of respective colors. When, for example, LEDs of the three primary colors are used, a color controller including R-, G- and B-dimming controllers for the respective colors can change the color of the light arbitrarily. If the gazing point illuminating device is used in a surgical operation or in a home medical care, the illuminance and the color can be changed easily as the operator desires. In some important cases, during a surgical operation, a slight color change of the light from the gazing point illuminating device will render clear difference in color of two parts showing similar colors otherwise.

The dimming control of the LEDs can be effected by a knob or the like. Alternatively, it may be effected by a voice recognition device which responds to the user's voice of verbal order, such as "on", "off", "light up" or "light down".

In an example of the present invention, the gazing direction detector determines the gazing direction of an eye by detecting a reflection of light projected to an eyeball. In one method, the gazing direction is detected from the distribution of the light reflected by the surface of the eyeball. In another method, a beam of light is projected to an eyeball and the direction of the reflected beam is detected.

In the present invention, the direction changing mechanism may change the lighting direction by tilting the light source vertically and/or horizontally. In this way, the lighting direction can be changed according to the gazing direction.

Alternatively, in the present invention, the direction changing mechanism may include a lens for refracting the light from the light source. The lens is tilted vertically and/or horizontally so that, as described above, the lighting direction can be changed corresponding to the gazing direction.

The gazing point illuminating device of the present invention may be attached to the user's body such as chest or abdomen, or it may be settled at a certain place of a room. It is also possible that the gazing point illuminating device of the present invention is attached to goggles or eyeglasses. When the goggles or eyeglasses according to the present invention are worn by a user, the user's shadow will never be cast on the gazing point. This is especially suited for use in a surgical operation. Besides the normal function of goggles to prevent blotting of blood or other stains on the wearer's eyes, they assure clear illumination of the part of operation without demanding a clumsy posture of the operator during an operation. As several people including the operator and the staff gaze the part of operation, the part is illuminated by the goggles of the people from diverse directions so that the illuminance is stronger and shadowing is more effectively avoided. Further advantage is that the goggles or eyeglasses are portable, which enables them to be easily used in home medical care or other field medical or nursing care. Conventional lighting devices could not have done it.

In another style of the present invention, two sets of light sources are provided corresponding to the left and right eyes. In this case, the gazing direction detectors detect the gazing directions of the left and right eyes independently, and the controller control the direction changing mechanism to change respective light sources' lighting directions corresponding to the detected left and right gazing directions. Since normally the left and right eyes' gazing lines cross at the gazing object, a greater illuminance and shadow-free illumination is obtained at the gazing object. As far as two sets are controlled as above, more than two light sources may be employed, of course.

The two light sources may be placed at the left and right ends of the front face of goggles. This style neatly utilizes the free space of the far ends of the goggles.

In this case, the gazing direction detector may determine the gazing direction by detecting the point on a piece of eyeshield of the goggles or on a piece of glass of the eyeglasses where the gazing line penetrates.

For example, the whole area of a piece of eyeshield or a piece of glass is divided into a plurality of sub-areas. Correspondingly, a plurality of lighting directions are predetermined for the light source. When one of the sub-area is determined where the gazing line of the eye penetrates, the controller brings the lighting direction of the light source to the direction corresponding to the detected sub-area. This is a rather simple way of detecting the gazing direction.

The surgical operation illuminating system of the present invention uses the gazing point illuminating device as described above, which detects the operator's gazing direction and change the lighting direction of the light source accordingly. In this system, the operator need not take a clumsy posture during an operation. The light source is always directed to the gazing object while the operator takes a variety of postures necessary for the operation. The accuracy of the operation will be improved greatly.

Above described gazing point illuminating devices are constructed so that they detect the user's gazing direction and change the lighting direction accordingly. When, however, the light source is attached to goggles or eyeglasses, the lighting direction normally accords with the gazing direction of the wearer, unless the wearer intentionally averts the eyes.

There have been so far many proposals for goggles or eyeglasses with a lamp or lamps. For example, Japanese Unexamined Utility Model Publication Nos. S56-156022 and S57-22720 disclose eyeglasses with a lamp at the center of the upper frame. Japanese Unexamined Utility Model Publication No. H6-7702 discloses eyeglasses for medical use to which an ordinary lamp is placed at the upper frame (paragraph [0021] of the publication). Japanese Utility Model Registration No. 3049423 discloses goggles for otolaryngologists which have lamps at the lower-left corner of the frame besides at the upper center. Japanese Unexamined Patent Publication No. 2000-39595 discloses eyeglasses with ordinary lamps on both temples.

However, none of them have been put into practical use. This can be ascribed to inadequate consideration into a proper selection of the light source and its location.

In the present invention, an LED panel or an EL panel, which are very compact and lightweight, are used for the light source. In case of an LED panel including a plurality of LEDs, the LEDs are arrayed one-dimensionally (straight or curve) or two-dimensionally. In case of an EL panel, an appropriate shape is cut out to fit the goggles or eyeglasses. The LEDs or EL panel are so lightweight that the goggles or eyeglasses according to the present invention weigh almost the same as ordinary ones without such a light source. Thus a practical gazing point illuminating device is realized by the present invention without causing fatigue to the wearer after wearing a long time. Among them, an LED panel is preferable because of its strong light, high efficiency and long life.

The LED panel or panels, or EL panel or panels, may be placed at the upper frame or lower frame of the goggles or eyeglasses. It is more preferable to attach them at the left and right ends of the front face of the goggles because they make a larger cross angle of the lighting directions which provides a better shadow-free illumination.

An LED has a high energy converting efficiency. When an LED or LEDs are used as the light source, heat generation is greatly reduced and the energy consumption is saved. The cost for a surgical operation illuminating system can be greatly reduced since the conventional large astral lighting system and a large cooling system are no more necessary.

For the portable use of LED-goggles, white LEDs can be driven, for example, by rechargeable Li-ion battery whose output voltage (current) can be controlled by a DC—DC converter.

According to the present invention, LEDs of the three primary colors, red, green and blue, are combined to provide light of a desired color. This enables a natural color appearance of the skin or blood. By using ultraviolet LED or LEDs, the application field is greatly expanded. For example, a fluorescent signing is put on a morbid part such as a tumor first in a preparatory examination. Then the morbid part can be recognized clearly during a subsequent operation.

In many road signs, fluorescent paint is used. The goggles or eyeglasses of the present invention using ultraviolet LED or LEDs can be preferably worn by a person walking or riding a bicycle at night. The fluorescent road signs can be recognized very obviously, which contributes greatly to the traffic safety.

Another useful situation is a night fishing. It is usually very difficult to perceive a motion of the float in a night fishing. In this case, similarly, the float can be made more clearly visible by making the float of fluorescent material or painting it with fluorescent paint, and then wearing goggles or eyeglasses using ultraviolet LEDs.

DETAIL DESCRIPTION OF PREFERRED EMBODIMENTS

Several embodiments of the present invention are described in detail referring to the attached drawings.

Embodiment 1

Figure 1:
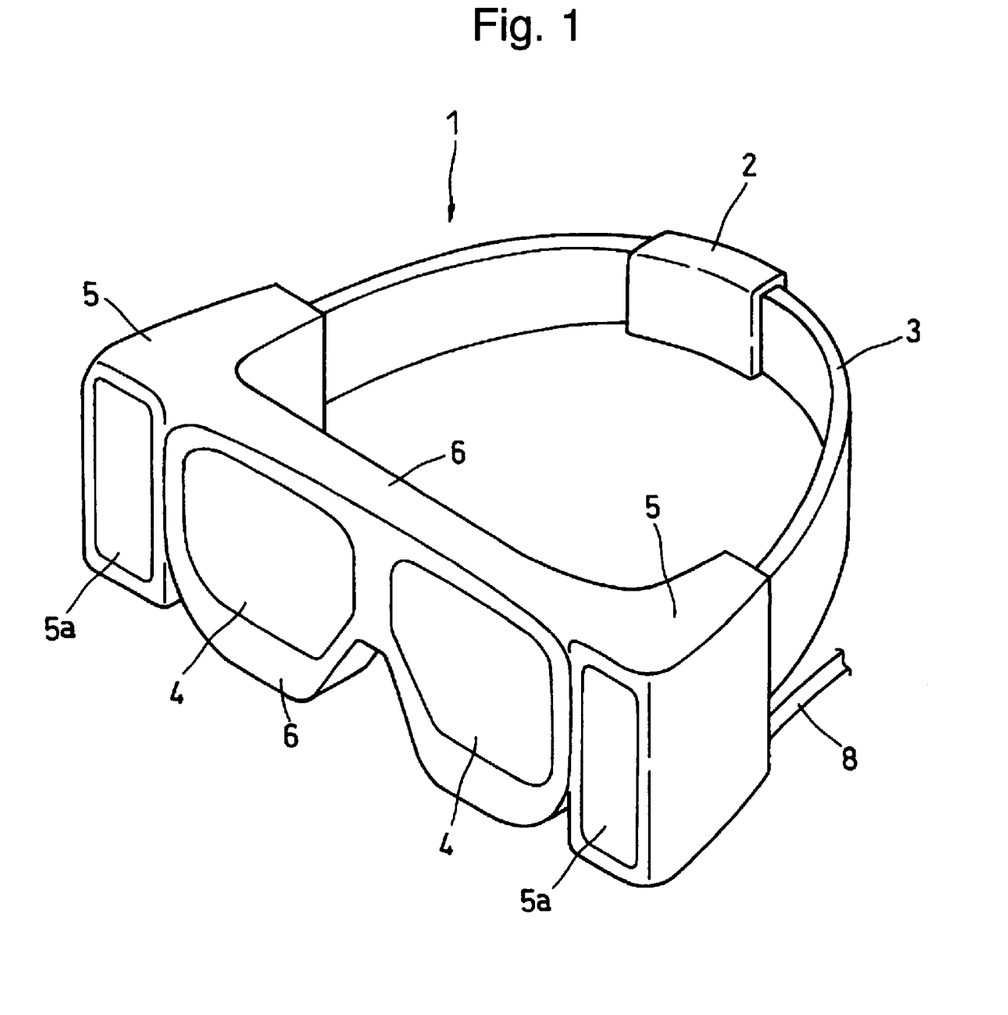
FIG. 1 is a perspective view of goggles embodying the present invention.
Figure 2:
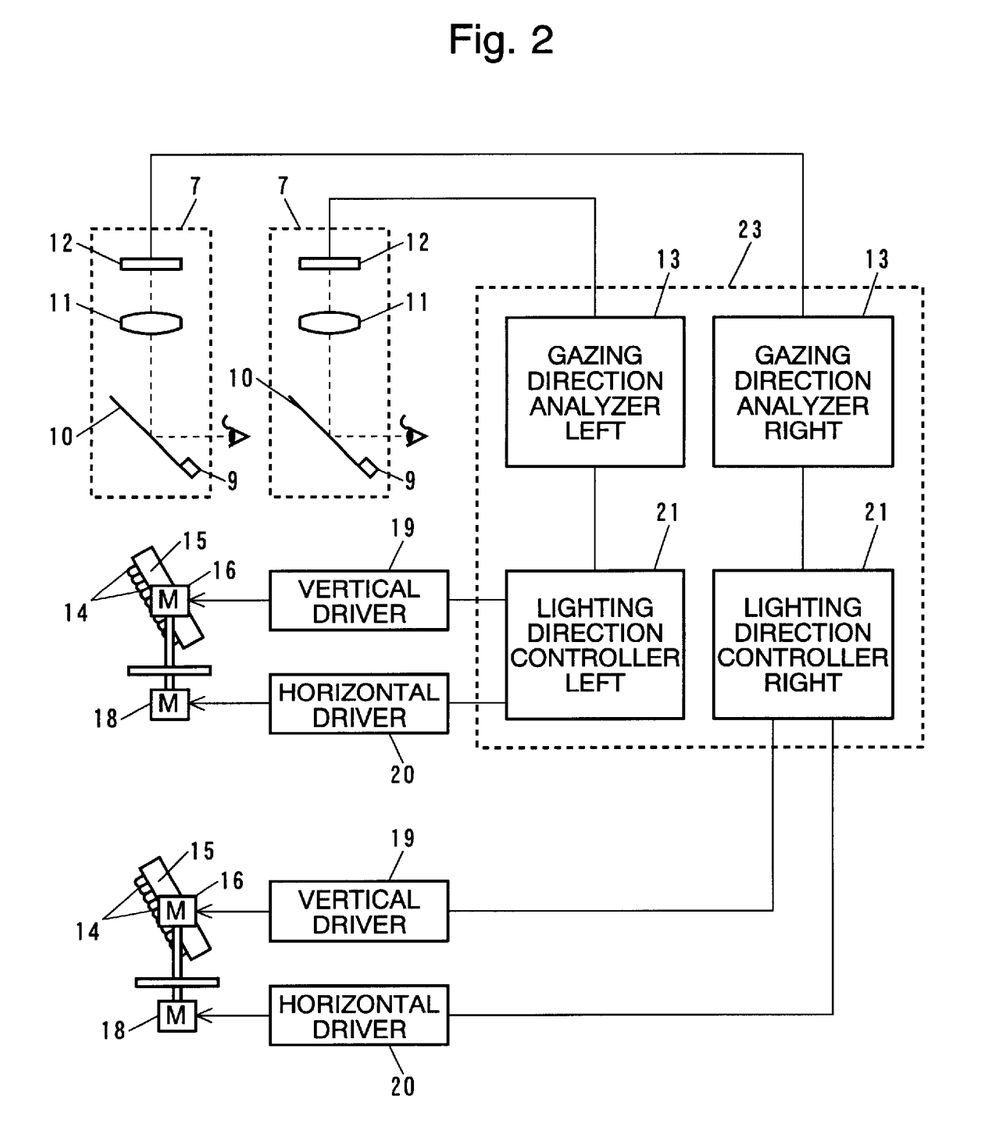
FIG. 2 is an abstract block diagram of the system of the above goggles.

FIG. 1 is a perspective view of an embodiment of the gazing point illuminating device of the present invention and FIG. 2 is an abstract block diagram of its system.

The gazing point illuminating device of the present embodiment is a pair of goggles 1 for medical use which an operator and staff wear during a surgical operation.

The goggles 1 of the present embodiment include a headband 3 equipped with an adjuster 2 for fitting the goggles 1 and headband 3 around the wearer's head, and a pair of transparent eyeshields or lenses 4, 4 for the left and right eyes. At each of the left and right ends of the goggles is provided with a housing 5, 5 for a light source, which will be described later. A transparent pane 5a, 5a is fixed at the front of each housing 5, 5. In the upper and lower beam of the frame 6 of the goggles 1, eye sensors 7 are provided, whose system is shown in the diagram of FIG. 2. A cord 8 is drawn out from one of the housings 5, 5 for connecting the light source, sensor, etc. to a switch and a battery pack (not shown). The switch and the battery pack can be attached to the goggle wearer's clothes or belt.

The battery pack may be attached to the goggles 1, in which case the cord can be omitted. Instead of using a battery pack, an AC/DC (alternating current to direct current) converter may be used. The shape of the panes 5a, 5a may be rectangular, circular or in any other shape, and a light diffuser may be provided in the panes 5a, 5a.

In the goggles 1 of the present embodiment, the gazing directions of the left and right eyes are detected independently, and the lighting directions of left and right light sources housed in the respective housings 5, 5 are automatically controlled independently according to the detected directions of the respective eyes.

Many types of gazing direction detectors have been devised so far. The present embodiment can employ any of such already known gazing direction detectors. For example, the Japanese Unexamined Patent Publication No. H8-46833 relates a conventional gazing direction detector as follows. Light from a light source, such as an infrared LED, is cast onto a wearer's eyeball, and the gazing direction of the eye is determined based on the relationship between the reflection of the light by the cornea and the image of the pupil.

The goggles 1 of the present embodiment use the same type of gazing direction detectors. As shown in FIG. 2, the goggles 1 are equipped with a pair of eye sensors 7 for the left and right eyeballs respectively. Each eye sensor 7 includes: an infrared LED 9 for casting infrared light to the eyeball; a dichroic mirror 10 which transmits visible light but reflects infrared light; a lens 11 for converging the infrared light reflected by the dichroic mirror 10; and an image sensor 12 which converts the infrared light converged by the lens 11 into electric signals. Corresponding to the eye sensors 7, gazing direction analyzers 13 are provided for the left and right eyes as shown in FIG. 2. Each of the gazing direction analyzers 13 determines the gazing point on a piece of eyeshield of the goggles based on the output signal from the corresponding eye sensor 7, or specifically saying, by analyzing the image of the wearer's eyeball taken by the image sensor 12.

The only difference of the gazing direction detector of the present embodiment from that related in the Japanese Unexamined Patent Publication No. H8-46833 is that the gazing point on the piece of eyeshield of the goggles is detected in the former while that on the finder plate of a camera is detected in the latter. The other structure is the same between them so that the detail description can be referred to in the prior art document.

Figure 3:
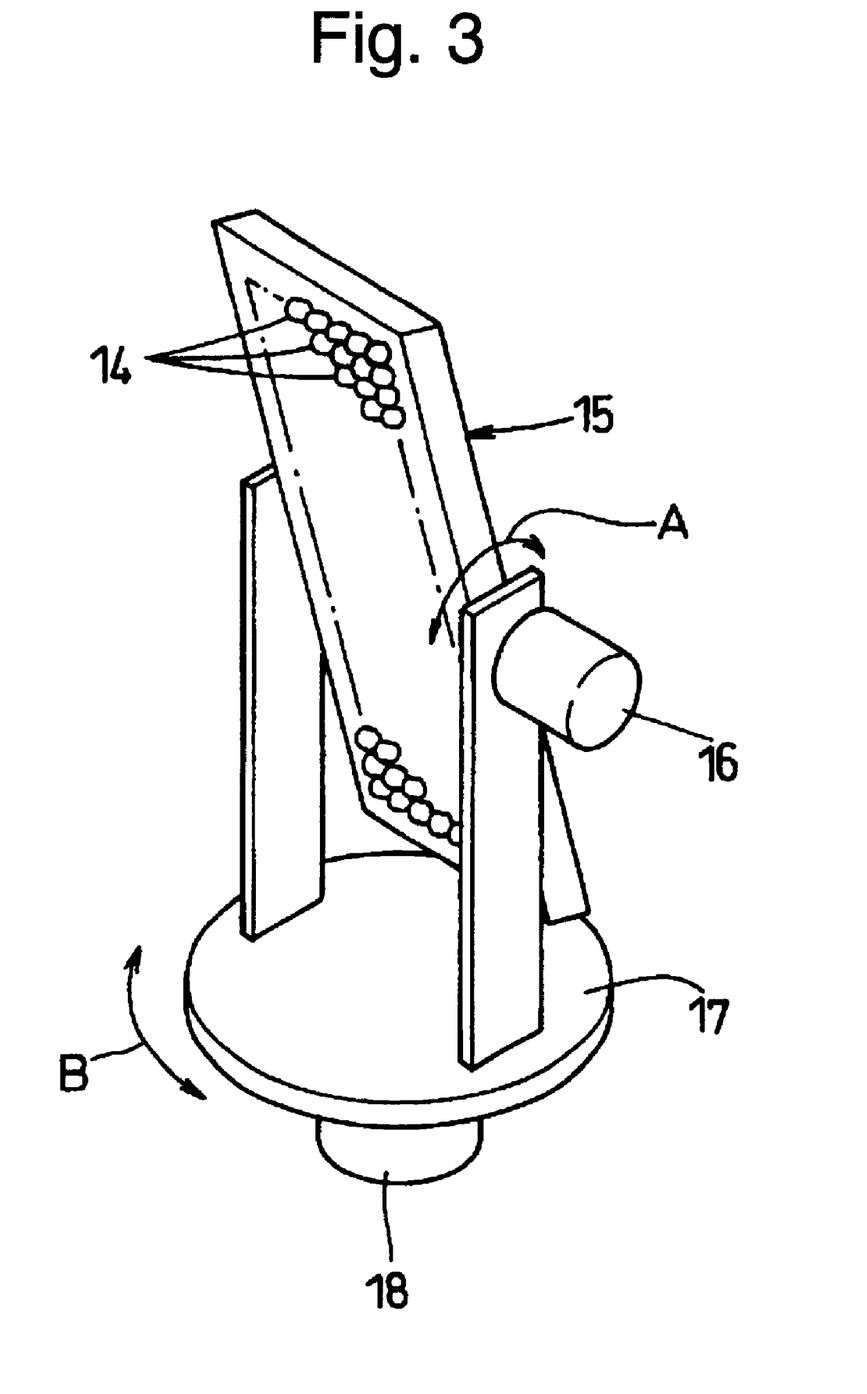
FIG. 3 is a perspective view of an LED panel and its driving mechanism.

In the present embodiment, the light source is an LED panel 15 on which many white LEDs 14 are arrayed two-dimensionally as shown in FIG. 3. An LED panel 15 is provided in each of the left and light housings 5, 5.

Currently, a white LED as strong as the luminous intensity of 3 candela is available. Using such strong white LEDs 14, for example, it is possible to illuminate an area of about 50 cm in diameter from about 50 cm distance. Preferably, white LEDs having appropriate directivity are used to intensify the light along the gazing direction. Alternatively, the base board of the LED panel 15 may be formed concave to converge the lights of the LEDs 14 to the gazing point.

In each of the left and right housings 5, 5, the LED panel 15 is rotated vertically and horizontally as shown in FIG. 3. Specifically, the LED panel 15 is rotated by a motor 16 about the horizontal axis (arrow A), and the base plate 17 on which the LED panel 15 and the motor 16 are supported is rotated by a motor 18 about the vertical axis (arrow B). For the motors 16 and 18, an ultrasonic motor or a stepping motor can be used. Since an LED panel 15 is driven by two motors 16 and 18, there are four motors 16 and 18 in a pair of goggles 1. The four motors 16 and 18 are respectively driven by corresponding driving circuits 19, 19 and 20, 20, as shown in FIG. 2. The motors 16 and 18 may be normal rotary motors, or alternatively, ultrasonic motors, piezoelectric motors, or other actuators.

Lighting direction controllers 21, 21 change the lighting direction of the left and right LED panels 15, 15 by controlling the motors 16, 16 and 18, 18 based on the detected gazing direction of the respective eyes, that is, the output of the gazing direction analyzers 13, 13. The gazing direction analyzers 13, 13 and the lighting direction controllers 21, 21 are included in a microcomputer 23.

Figure 4A:
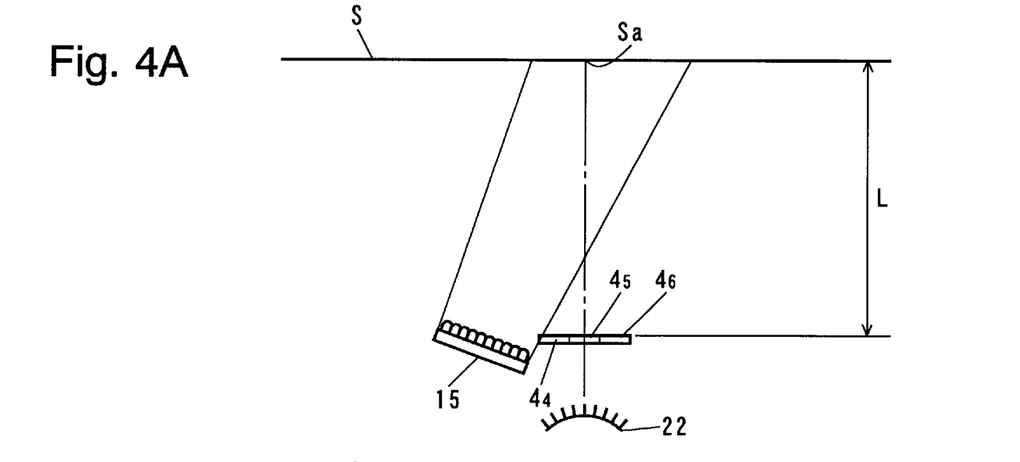
FIGS. 4A–4C are plan diagrams showing the relationship between the detected gazing direction and the lighting direction.
Figure 4B:
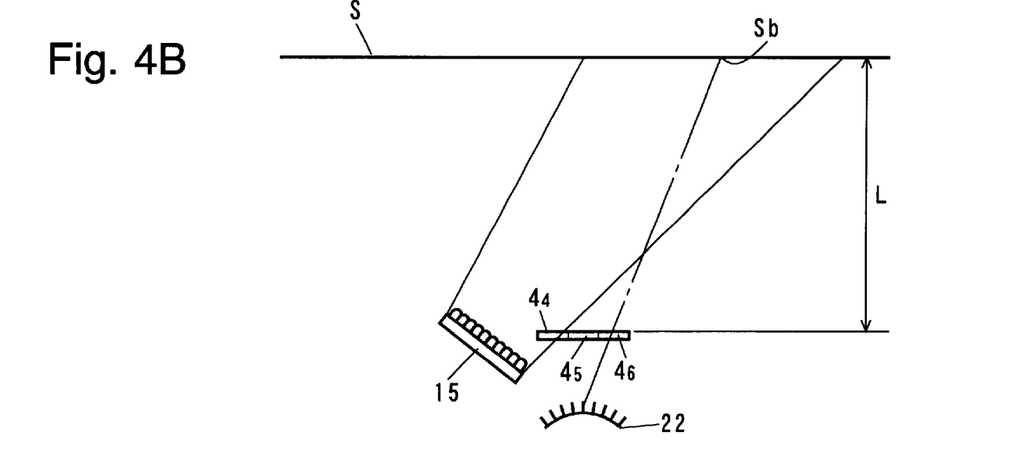
Figure 4C:
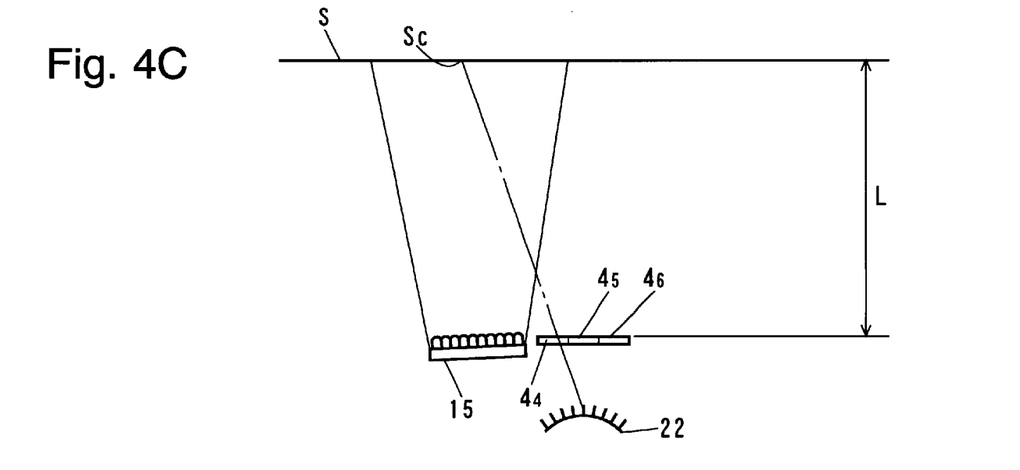
Figure 5:
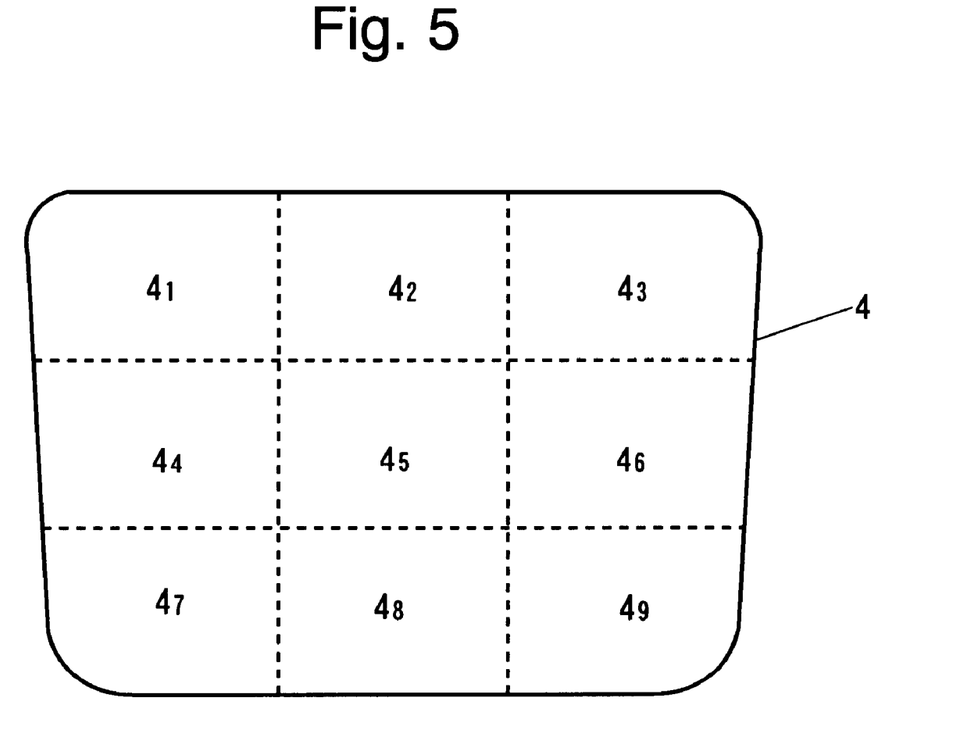
FIG. 5 shows a piece of eyeshield of goggles divided into a plurality of sub-areas.

The lighting direction controller 21, 21 controls the lighting direction as follows. FIGS. 4A–4C are diagrams showing the relationship between the gazing direction and the lighting direction of an LED panel 15 for an eye 22. In the present embodiment, the entire area of a piece of eyeshield 4 of goggles is divided into a plurality of sub-areas beforehand. In FIG. 5, the piece of eyeshield 4 is divided into nine sub-areas $4_1$–$4_9$ with three rows by three columns. The gazing direction analyzer 13 determines one of the nine sub-areas $4_1$–$4_9$ where the gazing line penetrates.

In each of the lighting direction controllers 21, 21, nine lighting directions corresponding respectively to the nine sub-areas $4_1$–$4_9$ are preset. Each of the lighting direction controllers 21, 21 brings the lighting direction of the corresponding LED panel 15 to that corresponding to the sub-area determined by the gazing direction analyzer 13.

The preset lighting directions are explained using FIGS. 4A–4C, which illustrate the horizontal plane at the center of a piece of eyeshield 4. It is supposed here, for simplicity, that the gazing line falls in one of the three sub-areas $4_4$, $4_5$, $4_6$ in the central row. The lighting directions are preset to illuminate a plane S which is distance L apart from the eyeshield 4 of the goggles. The distance L may be arbitrarily set, but in case of surgical operation, it is preferable to set the distance L at about 50 cm since the distance between the operator and the part of operation is about 46 cm in a standing operation and about 34 cm in a sitting operation.

When the gazing line penetrates the central sub-area 45 of the glass area 4 as shown in FIG. 4A, the lighting direction is set so that the LED panel 15 illuminates around the point Sa which is the foot of the gazing line passing through the center of the sub-area 45 on the plane S. When the gazing line penetrates the right sub-area 46 as shown in FIG. 4B, the lighting direction is set so that the LED panel 15 illuminates around the point Sb which is the foot of the gazing line passing through the center of the sub-area 46 on the plane S. Similarly, as shown in FIG. 4C, when the gazing line penetrates the left sub-area 44, the lighting direction is set so that the LED panel 15 illuminates the point Sc which is the foot of the gazing line passing through the center of the sub-area 44 on the plane S. Thus the nine lighting directions corresponding to the nine sub-areas $4_1$–$4_9$ as shown in FIG. 5 are preset. The preset is made for each of the right and left eyes.

With the nine lighting directions preset for each eye, each of the lighting direction controllers 21, 21 for the left and right eyes controls the vertical driving circuit 19 and the horizontal driving circuit 20 to change the orientation of the LED panel 15 to bring the lighting direction of the LED panel 15 to one of the nine preset lighting directions that corresponds to the determined sub-area of the eyeshield 4 based on the output from the corresponding gazing direction analyzer 13.

Thus from the left and right LED panels 15 of the goggles 1 worn by the operator and staff, beams of light are directed according to the wearer's left and right eyes' gazing directions.

The number of sub-areas of a piece of eyeshield 4 may be larger or smaller than nine as shown in FIG. 5. Further, the lighting direction of the LED panel 15 may be changed subtlier according to the coordinates of the point on the piece of eyeshield 4 that the gazing line penetrates. The distance L may be other than 50 cm, and further the distance L may be changed according to a distance detected by some distance measuring means.

Since the gazing point illuminating device of the present embodiment is goggles worn on the head, the wearer's shadow is never cast to the part of operation, so that the operator or the staff need not take a clumsy posture during a surgical operation. In addition to that, the illuminating point accords to their gazing point. Different from a conventional illuminating device where a lamp with a fixed lighting direction is worn on the operator's head, the wearer of the illuminating device of the present embodiment does not have to bend his/her head clumsily or unnaturally in order to illuminate a gazing point. This greatly alleviates fatigue and pains on the neck or shoulder of the wearer.

Since several people including the operator and staff gaze the part of operation during a surgical operation, the light from their goggles 1 jointly illuminate the part, which enables an efficient illumination.

A conventional astral lighting system which claims a large construction cost and cooling system is no more necessary. Because an LED has a high conversion efficiency, heat production of the light source is reduced and energy is saved. Longlife and low-cost are direct consequences of using LEDs.

Embodiment 2

Figure 6:
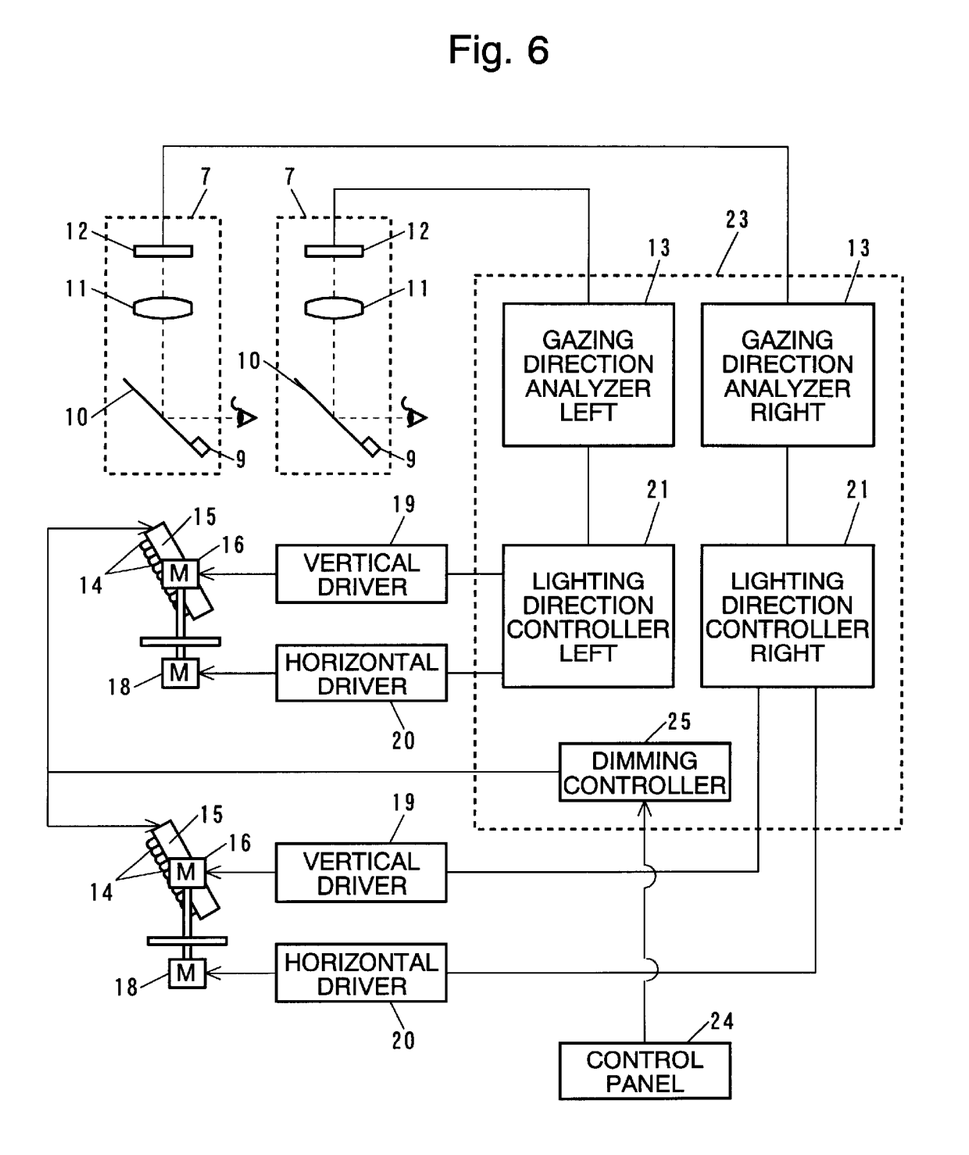
FIG. 6 is an abstract block diagram of the system of another embodiment of the present invention.

FIG. 6 is a block diagram of the system of another embodiment of the present invention. Same reference numerals are used for the parts corresponding to those in FIG. 2.

In this embodiment, a dimming controller 25 is provided for changing the driving current to the LEDs 14 of the LED panels 15, 15 responsive to a manual control on a control panel 24. Thus the illuminance can be controlled by a manual control from the control panel 24. This enables the operator or staff of a surgical operation wearing goggles 1 to change the illuminance at the part of operation according to his/her age, preference or other factors.

Other Embodiments

In the above embodiments, white LEDs are used as the light source. Alternatively, a collection of units composed of a red LED, a green LED and a blue LED (RGB LED units) can be used as the light source. In this case, it is possible to differentiate the driving currents to the LEDs of the three colors using respective dimming controllers or an integrated dimmer controller to change the color of the light.

The operator or staff wearing the goggles 1 can manipulate the control panel to change the color so that the color of organs or blood may look more natural. The illuminance can also be controlled.

Ultraviolet LEDs may be added to the light source of white LEDs or that of a collection of RGB LED units. The ultraviolet LEDs excite a fluorescent signing attached beforehand on a morbid part such as a tumor, and make the part conspicuously visible.

Figure 7:
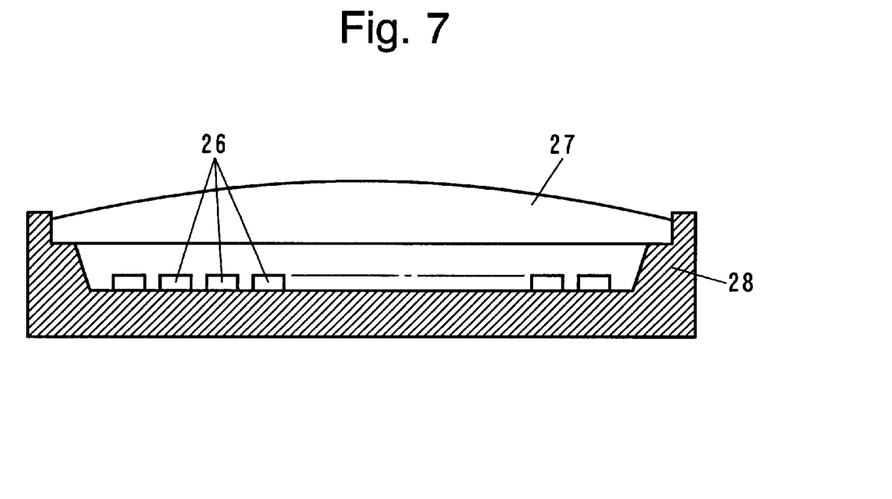
FIG. 7 is a sectional view of an LED panel of another embodiment of the present invention.

Another embodiment of the present invention uses a chip type LED panel. In a chip type LED panel, as described before, many LED chips are placed directly on a surface of a board. Since every LED is not packaged in a cannonball type plastic case, the LEDs can be closely arrayed in an LED panel. Therefore the light source can be made very small and lightweight. If necessary, as shown in FIG. 7, the LED chips 26 of a chip type LED panel 28 may be covered with a lens 27 or a diffuser.

Figure 8:
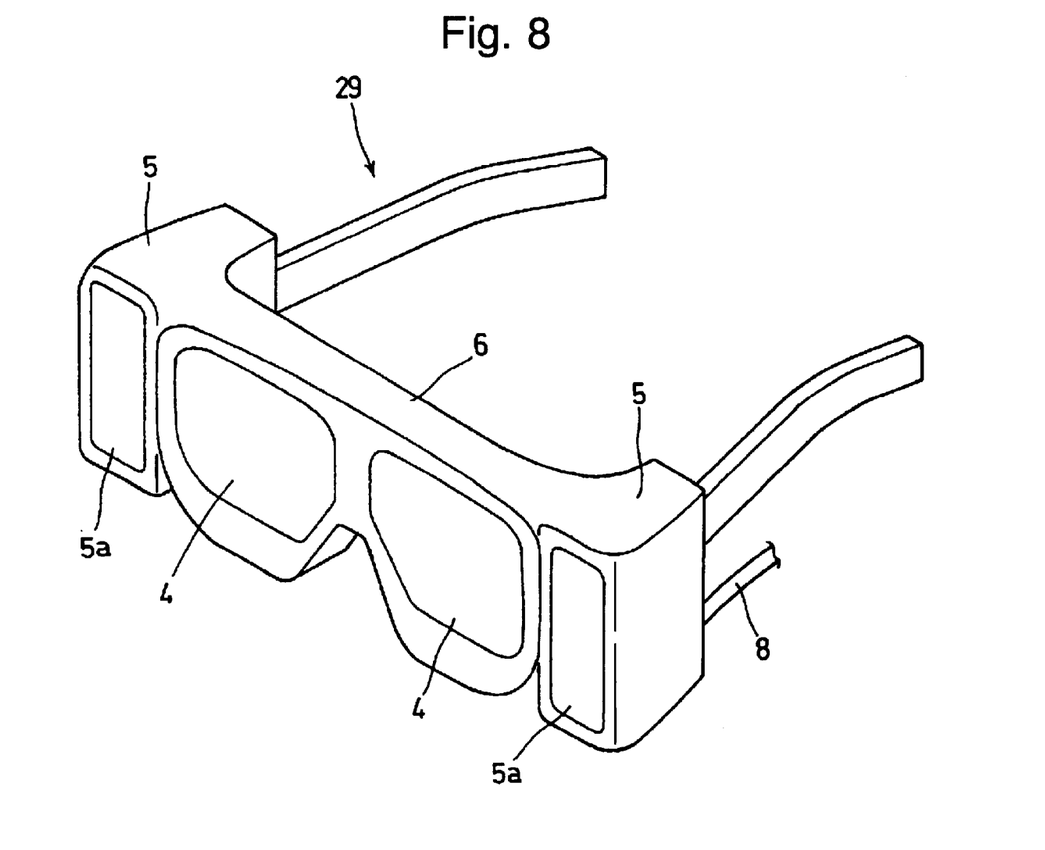
FIG. 8 is a perspective view of eyeglasses as another embodiment of the present invention.

Instead of the goggles 1 of FIG. 1, the present invention is applicable to goggle-type eyeglasses 29 as shown in FIG. 8.

In another embodiment of the present invention, a zoom mechanism is added to the gazing point illuminating device to zoom in or out the illumination on the part of operation. In another embodiment, a focus mechanism is added to the gazing point illuminating device to focus the light from the light source to the part of operation or to change the size of the illuminated area. In this case, the distance to the gazing object is measured beforehand by, for example, using an infrared distance sensor or an ultrasonic distance sensor, and a lens or a group of lenses is driven by a motor in the focus mechanism to focus the light to the gazing object according to the measured distance.

In addition to the two light sources respectively provided for the left and right eyes in the above embodiment, further light sources may be provided at the space of the upper or lower part of the goggles 4. Alternatively, it is also possible to provide a sole light source at the center of the goggles 4 and illuminate the gazing point at the intersection of the two eyes' gazing lines.

In the above embodiments, both eyes' gazing directions are detected independently. Because a person normally gazes an object with both eyes, it is also possible to detect the gazing line of an eye and illuminate the corresponding direction.

In the above embodiments, the lighting direction is changed by moving the light source. Alternatively, it is possible, with a fixed light source, to provide a lens or lenses in front of the light source, and move the lens or lenses to deflect and change the lighting direction.

In the above embodiments, the light source is worn by an operator or staff. Alternatively, the light source may be placed at an appropriate place of the operation room, and the operator or staff wear only the gazing direction detector. According to the gazing direction detected by the detector worn by the operator or staff, the lighting direction of the light source placed in the operation room is controlled.

In the above embodiments, the device of the present invention is applied in a surgical operation illuminating system. Of course the gazing point illuminating device of the present invention can be applied to home medical care purposes such as nursing care. Since the device of the present invention is portable as goggles, it is no more necessary to carry heavy lighting equipments as in a conventional home medical care situation. In such a situation, the diseased part requiring treatment is adequately illuminated by the goggle-type gazing point illuminating device worn by a doctor or nurse.

Further, the present invention can be applied to following uses. A night guard's lighting device, a night vision system, a special work requiring a spot light, goggles for fishing or ski at night, an illuminating device for scuba diving, for looking at exhibitions in a museum or plays in a theater, and various uses for entertainment, fashion or art.

In the above embodiments, an LED is used as the light source. A lamp other than an LED or a semiconductor laser may be used as the light source as well.

Figure 9:
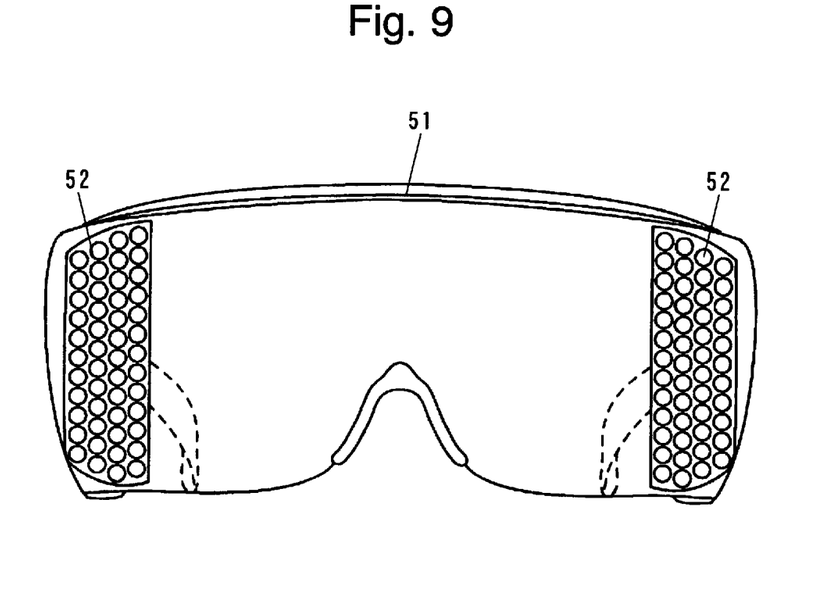
FIG. 9 is a front view of goggles as still another embodiment of the present invention.

In the above embodiments, gazing point or gazing line detectors are included. When, however, LEDs are used as the light source, and the light source is attached to the goggles or goggle-type eyeglasses worn by a user, the goggles or eyeglasses can be useful gazing point illuminating device by themselves even if they do not include gazing point or direction detectors. That is, a person normally looks straight ahead or his/her gazing direction is normally straight ahead when he/she works. Therefore, except for unusual occasions where he/she purposefully averts his/her gaze, an illuminating device fixed to a person's head for lighting forward is a gazing point illuminating device. Thus the goggles provided with an appropriate illuminating device without a gazing point detector or a lighting direction controller can be used as a gazing point illuminating device according to the present invention. In this case, it is preferable to place the LEDs 52 at the left and right ends of the goggles or glasses 51 as shown in FIG. 9.

The power source to the LEDs 52 may be an AC/DC converter connected to the wall socket or a battery worn by the wearer of the goggles or eyeglasses. A rechargeable Li-ion battery is preferred in this use whose output voltage (current) can be controlled by a DC—DC converter.

Figure 10:
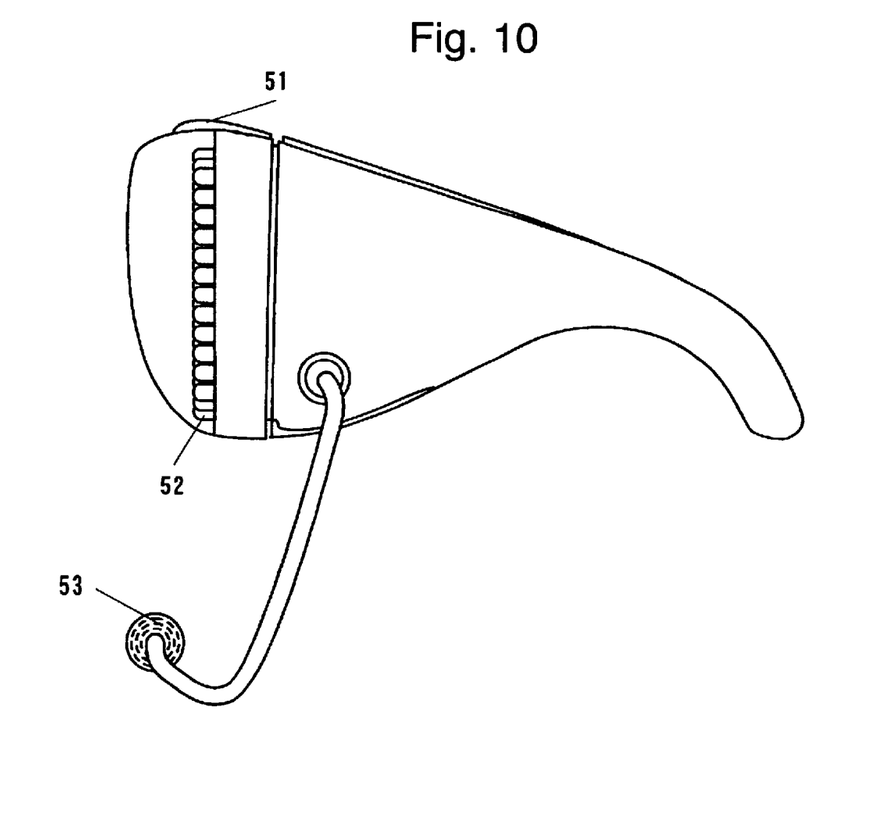
FIG. 10 is a side view of the above goggles with a voice controlled gazing point illuminating device.

It is further preferable to make the lighting strength of the LEDs controllable. For controlling the lighting strength, a manual knob may be provided on a temple of the goggles or glasses. Alternatively, a voice control system may be used. The user gives a verbal command (for example, "on"/"off", "up"/"down") through a microphone 53 attached to the goggles, as shown in FIG. 10, to a voice recognition circuit and LED controller incorporated in the goggles or glasses.

Instead of the automatic lighting direction controller used in the previous embodiments, it is preferable to make the LED panel (or panels when they are attached at both ends of the goggles or eyeglasses) manually tiltable. In this case, a small tilting knob or handle may be provided to the frame of the goggles or eyeglasses so that the wearer can easily change the illuminating point according to his position in relation to the gazing object.

In place of an LED panel, an EL panel can be used. In any case, the weight of the goggles or goggle-type eyeglasses including such an illuminating device is almost the same as that of an ordinary goggles, so that they can be used as a practical gazing point illuminating device which can be worn for a long time.

As described above, in one feature of the present invention, the gazing direction of a user is detected and the lighting direction is changed according to the detected gazing direction, so that the gazing point is automatically illuminated.

In another feature of the present invention, an LED panel composed of a plurality of arrayed LEDs is used as the light source. This decreases heat generation of the light source and the energy consumption is saved compared to conventional incandescent lamps. Another advantage is that it makes the illuminating device of the present invention lightweight and longlife.

Using an LED panel composed of red, green and blue LEDs, and adjusting the intensity of every color, the user can obtain an illumination of a desired color When the illuminating device of the present invention is used in a surgical operation, the light is automatically directed toward the gazing point of the operator while the operator does not need to take a clumsy posture. This greatly reduces the cost of a surgical operation illuminating system. Conventional astral lighting system which claims a high construction cost of the operation room and a large scale cooling system is no more necessary.

When the illuminating device of the present invention is used in a surgical operation or in medical or home care situations, it is possible to adjust the color of the illumination so that the color of the skin, internal organ or blood looks natural. When ultraviolet LEDs are used, further, only a morbid part such as a tumor can be made visible by attaching a fluorescent signing on such a part.

What is claimed is:

1. A gazing point illuminating device comprising an LED panel including one or a plurality of LEDs attached to goggles or eyeglasses, wherein an LED panel is placed at each of a left end and a right end of the goggles or eyeglasses.

2. The gazing point illuminating device according to claim 1, wherein the LED panels are tiltable.

3. The gazing point illuminating device according to claim 1, wherein the LED panel includes one or a plurality of white LEDs.

4. The gazing point illuminating device according to claim 1, wherein the LED panel includes one or a plurality of sets consisting of a red LED, a green LED and a blue LED.

5. The gazing point illuminating device according to claim 1, wherein the LED panel includes one or a plurality of ultraviolet LEDs.

6. The gazing point illuminating device according to claim 1, wherein the LED panel includes one or a plurality of chip type LEDs.

7. The gazing point illuminating device according to claim 1, wherein a power source to the LED or LEDs is a battery wearable to a wearer of the goggles or eyeglasses.

8. The gazing point illuminating device according to claim 1, wherein the gazing point illuminating device further comprises dimming means for controlling a lighting strength of the LED or LEDs.

9. The gazing point illuminating device according to claim 8, wherein the dimming means comprise a voice recognition device to change the lighting strength of the LED or LEDs according to the user's verbal command.

10. The gazing point illuminating device according to claim 8, wherein a power source to the LED or LEDs is a battery wearable to a wearer of the goggles or eyeglasses.

* * * * *